(12) United States Patent
Dixon et al.

(10) Patent No.: US 12,247,189 B1
(45) Date of Patent: Mar. 11, 2025

(54) TEER ELECTRODE ALIGNMENT MOUNT

(71) Applicant: Government of the United States, as represented by the Secretary of the Air Force, Wright-Patterson AFB, OH (US)

(72) Inventors: Angela Dixon, Beavercreek, OH (US); Dana Powers, Beavercreek, OH (US); Saber Hussain, Beavercreek, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 644 days.

(21) Appl. No.: 17/341,562

(22) Filed: Jun. 8, 2021

Related U.S. Application Data (60) Provisional application No. 63/071,083, filed on Aug. 27, 2020.

(51) Int. Cl.
  *C12M 1/00* (2006.01)
  *C12M 1/32* (2006.01)
  *C12M 1/34* (2006.01)

(52) U.S. Cl.
  CPC ............ *C12M 23/50* (2013.01); *C12M 23/12* (2013.01); *C12M 41/46* (2013.01)

(58) Field of Classification Search
  CPC ....... C12M 23/50; C12M 23/12; C12M 41/46
  USPC ...................................................... 435/283.1
  See application file for complete search history.

(56) References Cited

U.S. PATENT DOCUMENTS 7,459,303 B2   12/2008  Wang
9,861,812 B2 *  1/2018  Gross ................... A61N 1/0556

FOREIGN PATENT DOCUMENTS

DE         10108968 A1 *  9/2000  ............ C12M 35/02
EP          2302353 A1    3/2011
WO      WO2018157073 A1    8/2018

OTHER PUBLICATIONS

DE10108968A1 Translation (Year: 2002).*

* cited by examiner

*Primary Examiner* — Michael L Hobbs
*Assistant Examiner* — Lenora A Abel
(74) *Attorney, Agent, or Firm* — AFMCLO/JAZ; Matthew D. Fair (57) ABSTRACT

The present disclosure generally relates to an alignment mount for electrode device used to measure transepithelial/transendothelial electrical resistance (TEER) for cell culture models of endothelial and epithelial monolayers. The TEER electrode alignment mount includes a base having a top wall, a bottom wall and a sidewall shaped to fit within a culture tray chamber. An extension arm projects from a top wall of the base. A pair of through apertures are formed in the base on opposing sides of the arm to receive first and second electrodes therethrough, respectively. An optional adjustable sliding sleeve for changing the height of the arm can be selectively coupled to the extension arm.

16 Claims, 5 Drawing Sheets

TEER ELECTRODE ALIGNMENT MOUNT

RIGHTS OF THE GOVERNMENT

The invention described herein may be manufactured and used by or for the Government of the United States for all governmental purposes without the payment of any royalty.

TECHNICAL FIELD

The present disclosure generally relates to an alignment mount for chopstick electrodes used to measure transepithelial/transendothelial electrical resistance (TEER) for cell culture models of endothelial and epithelial monolayers.

BACKGROUND

Transepithelial/transendothelial electrical resistance (TEER) is a widely accepted quantitative technique to measure the integrity of tight junction dynamics in cell culture models of endothelial and epithelial monolayers. TEER values are strong indicators of the integrity of the cellular barriers before they are evaluated for transport of drugs or chemicals. TEER measurements can be performed in real-time without cell damage and generally are based on measuring electrical resistance or impedance across a wide spectrum of frequencies. TEER measurements for various cell types have been used with commercially available measurement systems and with custom built microfluidic implementations. Some of the barrier models that have been widely characterized utilizing TEER include the blood-brain barrier (BBB), gastrointestinal (GI) tract, and pulmonary models.

Endothelial cells provide a nonthrombogenic monolayer surface that lines the lumen of blood vessels and functions as a cellular interface between blood and tissue. Epithelial cells line and provide a protective layer for both the outside and the inside cavities and lumen of the body. Epithelial and endothelial cells are connected to each other via intercellular junctions that differ in their morphological appearance, composition and function. The tight junction or zona occludens is the intercellular junction that regulates diffusion and allows both of these cell layers to form selectively permeable cellular barriers that separate apical (luminal) and basolateral (abluminal) sides in the body, thereby controlling the transport processes to maintain homeostasis. Barrier integrity is vital for the physiological activities of the tissue. To successfully treat certain diseases of organs protected by physiological barriers, it is necessary to develop methods that can enable the transport of therapeutic drugs across these barriers in order to reach the target tissue.

Barrier systems for predicting drug permeability typically include cell cultures grown on permeable membranes. The configuration in these systems is designed to allow access to both apical and basolateral compartments. These models primarily include cells that grow in a monolayer when seeded on permeable membranes, and have physiologic characteristics similar to the barrier physiology and functionality. The successful application of a system to predict drug absorption depends on how closely the in vitro model can mimic the characteristics of the in vivo barrier integrity. These in vitro models can be based on primary cells or cell lines.

Transepithelial electrical resistance measurements can be taken with the electrodes to determine the integrity of a cell sheet that is cultured on a culture tray for biological or biomedical research. In one form the culture tray can be a Transwell®. A Transwell® is commonly used by those skilled in art for a multi chamber tray culture lab work. Culture trays include lower and upper chambers separated by a tapered basket. The upper chamber consists of a membrane on which cells are seeded while the lower chamber can hold media that will feed the cells from the bottom.

Prior to the disclosed invention, the electrodes were stabilized by hand (e.g. handheld) in the culture tray chamber with the longer electrode touching the bottom well and the shorter electrode hovering just above the upper membrane. Accurate and consistent TEER readings require that the electrode probes be positioned perpendicular to the benchtop or wells. Several disadvantages are incurred by a user who positions the probe by hand when acquiring TEER readings. First, it may be difficult to ensure that the chopstick electrodes are precisely placed perpendicular to the benchtop every trial, which creates both inter and intra-researcher variability. Second, the probe is not guaranteed to be placed in the same relative spot between the culture tray support and the well wall, resulting in some readings being taken at variable distances from the edge of the culture tray support. Third, variability may be introduced by slight involuntary hand movements made while the researcher is taking TEER readings, as it can take several seconds for the EVOM2 machine to settle on a true resistance value. The inherent intra-user variability associated with how a researcher positions the electrodes in the wells can lead to a variability in electrical resistance measurements that ranges from 10-30 percent. For these and other reasons existing systems have various shortcomings, drawbacks, and disadvantages relative to certain applications. Accordingly, there remains a need for further contributions in this area of technology.

SUMMARY

One embodiment of the present disclosure includes a unique alignment fixture to hold, align, and stabilize chopstick electrodes while a researcher acquires TEER readings in a laboratory setting. Other embodiments include apparatuses, systems, devices, hardware, methods, and combinations wherein electrodes are connected to an apparatus to hold them in a desired location with respect to a culture tray chamber or cup. Further embodiments, forms, features, aspects, benefits, and advantages of the present application shall become apparent from the description and figures provided herewith.

DETAILED DESCRIPTION OF THE ILLUSTRATIVE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present disclosure defines an apparatus, system and method for reducing variance in transepithelial electrical resistance (TEER) measurements when using two electrodes sometimes called chopstick style electrodes. The device is configured to locate and stabilize device the electrodes such that a desired alignment is maintained while TEER measurements are made. The device ensures that the electrodes are positioned in the same relative location and angle in each well or chamber of the culture tray while also eliminating movement generated by the researcher during the TEER measurement period. In this manner, the present invention reduces the high intra-user and inter-user variability in TEER readings that is currently experienced in this research area.

Transepithelial/transendothelial electrical resistance (TEER) is the measurement of electrical resistance across a cellular monolayer and is a very sensitive and reliable method to confirm the integrity and permeability of the monolayer. Although the measurement of TEER and of trans-epithelial passage of marker molecules are both indicators of the integrity of the tight junctions and of the cell monolayer, they determine different experimental parameters. TEER reflects the ionic conductance of the paracellular pathway in the epithelial monolayer, whereas the flux of non-electrolyte tracers (expressed as permeability coefficient) indicates the paracellular water flow, as well as the pore size of the tight junctions. The advantage of the TEER method is that it is a non-invasive technique and can be applied to monitor live cells during their various stages of growth and differentiation.

The electrical resistance of a cellular monolayer, measured in ohms, is a quantitative measure of the barrier integrity. Measurement of TEER includes a cellular monolayer cultured on a semipermeable filter insert which defines a partition for apical (or upper) and basolateral (or lower) compartments or chambers. For electrical measurements, two electrodes are used, with one electrode placed in the upper chamber and the other in the lower chamber and the electrodes are separated by the cellular monolayer. In theory, the ohmic resistance can be determined by applying a direct current (DC) voltage to the electrodes and measuring the resulting current. The ohmic resistance is calculated based on Ohm's law as the ratio of the voltage and current. However, DC currents can damage both the cells and the electrodes. To overcome this issue, an alternating current (AC) voltage signal with a square waveform can be applied. The measurement procedure includes measuring the blank resistance (RBLANK) of the semipermeable membrane only (without cells) and measuring the resistance across the cell layer on the semipermeable membrane (RTOTAL). The cell specific resistance (RTISSUE) in units of 2, can be obtained as:

$$R_{TISSUE}(\Omega) = R_{TOTAL} - R_{BLANK}$$

Where resistance is inversely proportional to the effective area of the semipermeable membrane (MAREA) which is reported in units of cm².

$$R_{TISSUE}(\Omega) \propto \frac{1}{M_{AREA}(\text{cm}^2)}$$

TEER values are typically reported (TEERREPORTED) in units of $\Omega \cdot \text{cm}^2$ and calculated as:

$$\text{TEER}_{REPORTED} = R_{TISSUE}(\Omega) \times M_{AREA}(\text{cm}^2)$$

Impedance spectroscopy when combined with a fitting algorithm provides a more accurate representation of TEER values than traditional DC/single frequency AC measurement systems. Impedance spectroscopy is performed by applying a small amplitude AC excitation signal with a frequency sweep and measuring the amplitude and phase response of the resulting current.

Electrical impedance (Z) is the ratio of the voltage-time function V (t) and the resulting current-time function I (t):

$$Z = \frac{V(t)}{I(t)} = \frac{V_o \sin\theta}{I_o \sin(2\pi ft + \phi)} = \frac{1}{Y}$$

$$Z = Z_R + jZ_I$$

where Vo and Io are the peak voltage and current, f is the frequency, t is the time, $\phi$ is the phase shift between the voltage-time and current-time functions, and Y is the complex conductance or admittance. Z is a complex function and can be described by the modulus Z and the phase shift $\phi$ or by the real part $Z_R$ and the imaginary part $Z_I$.

Impedance measurement across a wide spectrum of frequencies instead of a DC/single frequency AC TEER measurement can provide additional information about the capacitance of the cell layer. An equivalent circuit analysis of the measured impedance spectrum is performed to obtain the electrical parameters that can be applied to characterize the cellular barrier properties. The electrical current can flow through the junctions between cells (paracellular route) or through the cell membrane of the cells (transcellular route). The tight junction proteins in the paracellular route contribute to an ohmic resistance (RTEER) in the equivalent circuit. Each lipid bilayer in the transcellular route contributes to a parallel circuit consisting of ohmic resistance (Rmembrane) and an electrical capacitance (CC). In addition to these elements, the resistance of the cell culture medium (Rmedium) and the capacitance of the measurement electrodes (CE) also have to be considered. The high values of Rmembrane causes the current to mostly flow across the capacitor and allows an approximation where Rmembrane can be ignored and the lipid bilayers can be represented with just CC.

TEER values are accepted as strong indicators of the integrity of the cellular barriers before they are evaluated for transport of drugs or chemicals. Impedance spectroscopy, in combination with equivalent circuit analysis, provides a more accurate representation of TEER values than the DC/single frequency AC measurement approach. The use of cells cultured under static conditions on permeable membranes of standard cell culture inserts with external electrodes is predominant. The models for drug development depends on how closely they mimic the complexity of drug absorption of the in vivo barriers.

Figure 1:
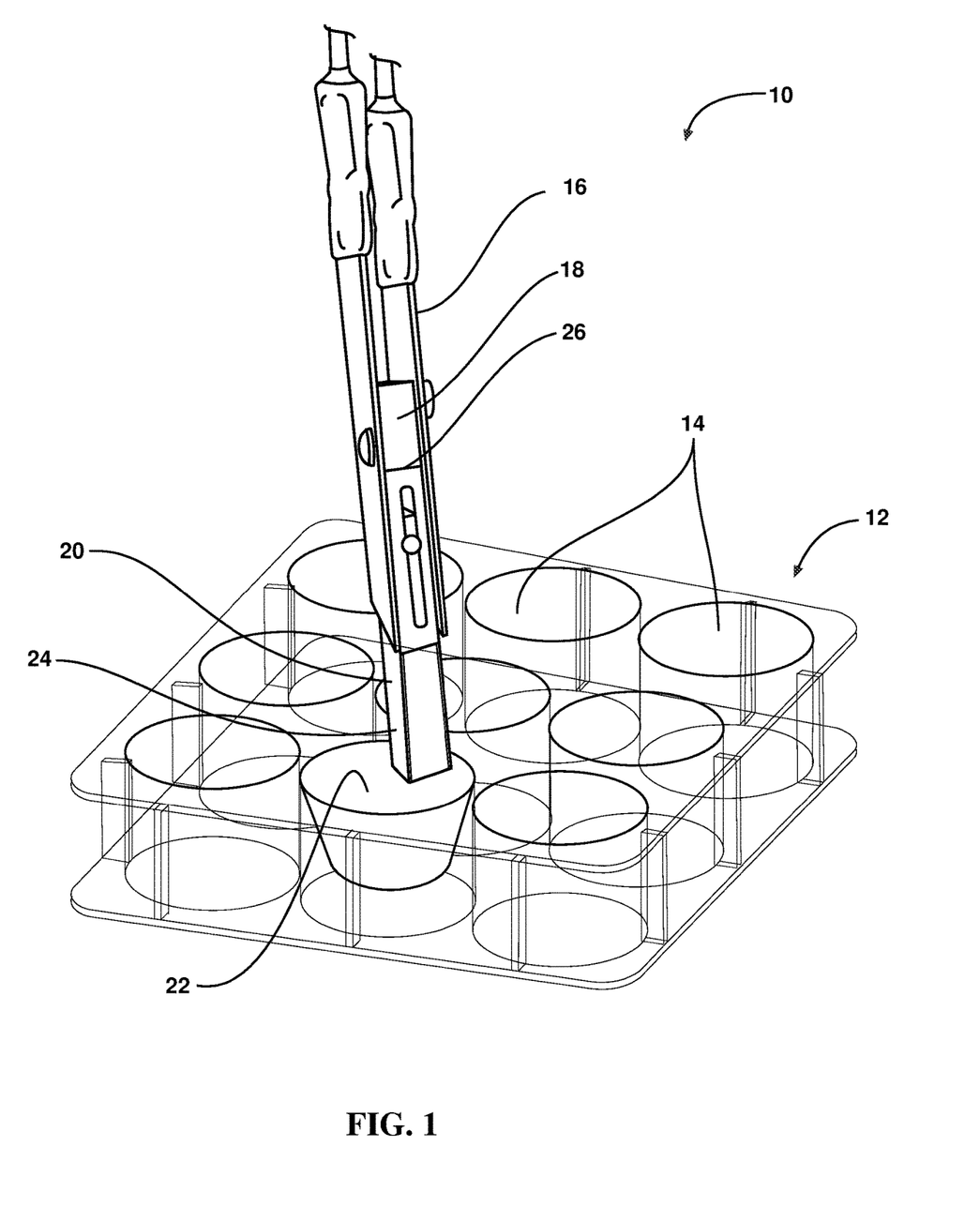
FIG. 1 is a schematic illustration of a TEER measurement system according one embodiment of the present disclosure.

Referring now to FIG. 1, a TEER measurement system 10 is illustrated in schematic form. The TEER measurement system 10, includes a culture tray 12 with at least one culture tray chamber 14 or as illustrated in the disclosed embodiment a plurality of culture tray chambers 14. A pair of chopstick electrodes 16 include an electrode abutment plate 18 that is configured to engage an electrode alignment mount 20. The alignment mount 20 includes a base 22 for resting within a culture tray chamber 14 and an arm 24 extending from the base 22. The arm 24 includes a mount top wall 26 configured to receive contact with the abutment plate 18 of the electrode device 16.

Figure 2:
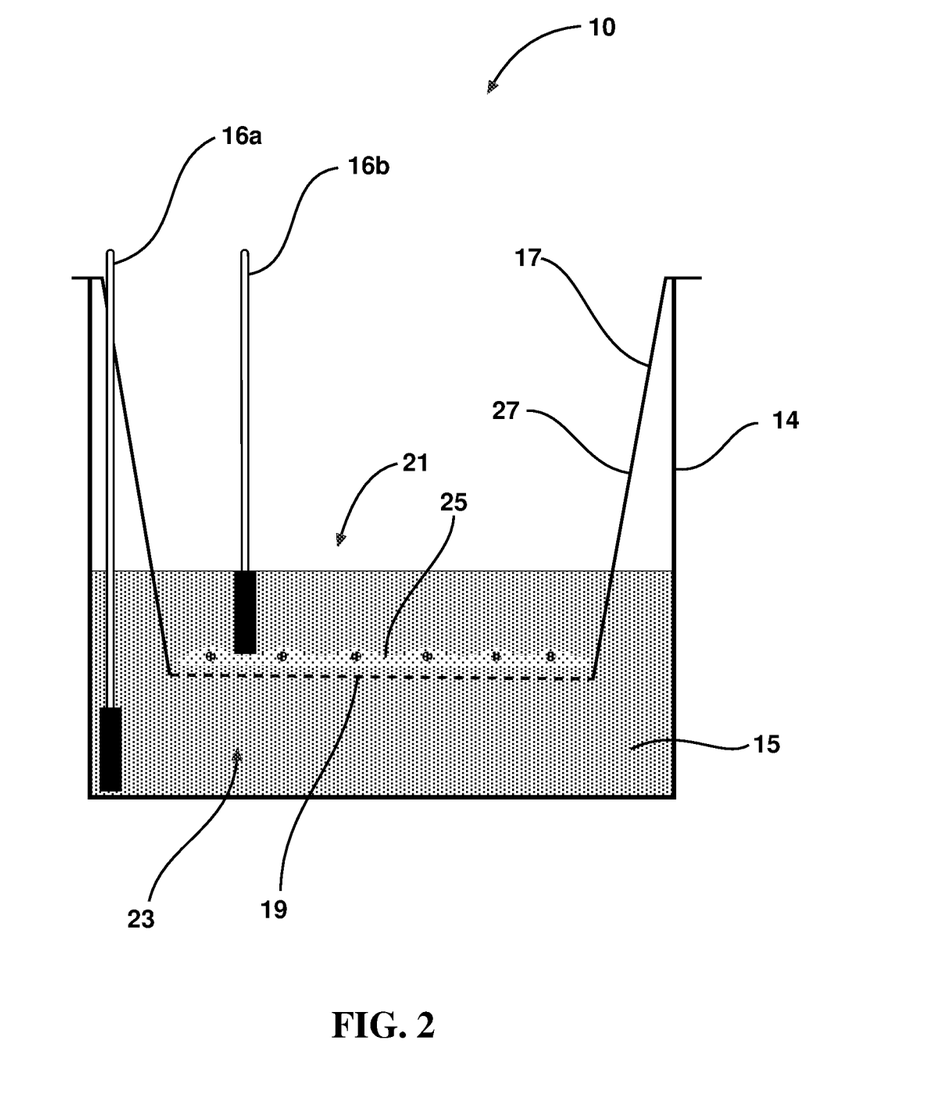
FIG. 2 is a schematic cross-sectional view of a portion of the TEER measurement system of FIG. 1 with electrodes positioned in a culture tray chamber.

FIG. 2 is a schematic cross-sectional view of a portion of the TEER measurement system 10 including a culture tray chamber 14 with electrodes 16a and 16b positioned therein. The culture tray chamber 14 includes a well basket 17 that in some forms can include a semipermeable membrane floor 19 and a tapered sidewall 27. A culture medium 15 is disposed in the culture trey chamber 14 and is separated into an upper chamber 21 and a lower chamber 23 delineated by the floor 19 of the well basket 17. A layer of cells 25 is placed on the floor 19 of the well basket 17. The first electrode 16a is placed in the lower chamber 23 of the culture trey chamber 14 and the second electrode is placed in the upper chamber 21 proximate the layer of cells 25. Electrical differential measurements can then be made between the cell layer 25 and the culture medium 15.

Figure 3A:
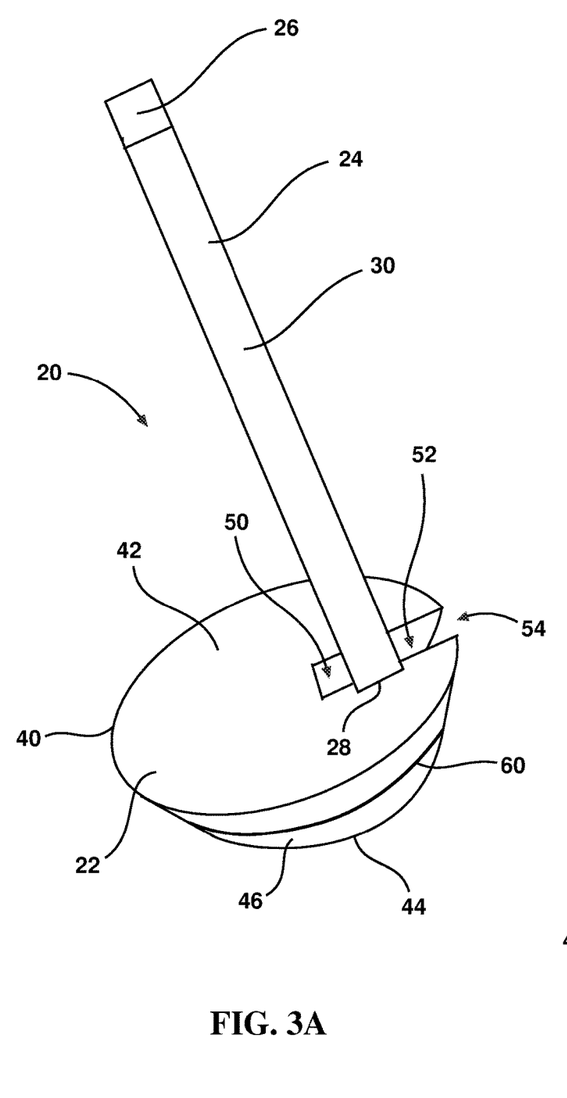
FIGS. 3A and 3B are perspective views of an alignment mount according one embodiment of the present disclosure.
Figure 3B:
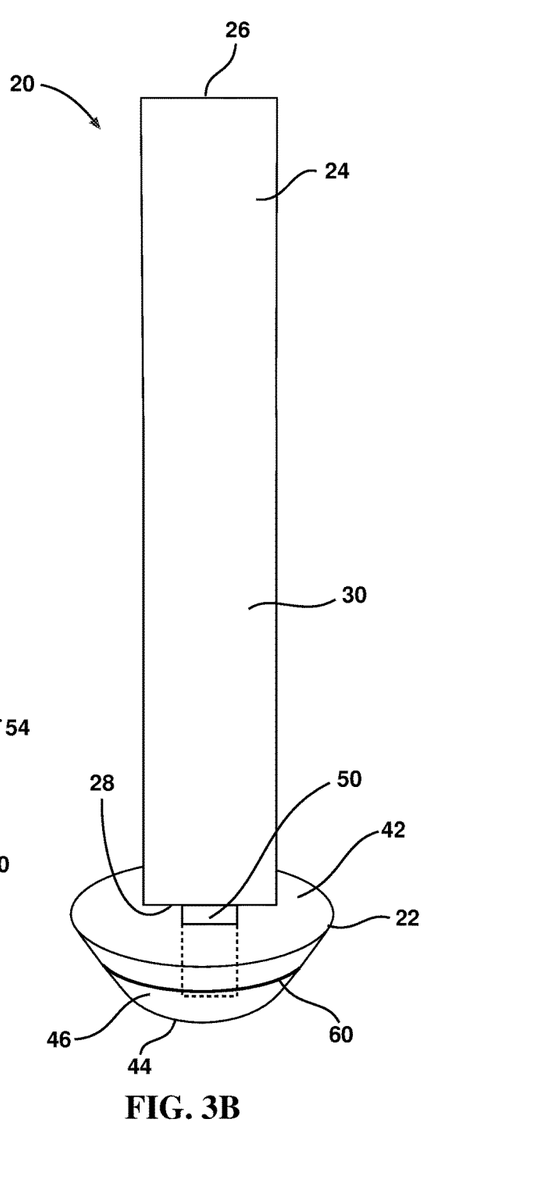

Referring now to FIGS. 3A and 3B, perspective views of an alignment mount 20 according to one embodiment of the present disclosure is illustrated. As explained above, electrical measurement of the cells 25 is more effective if the electrodes 16a and 16b are consistently positioned in the same relative orientation. The alignment mount 20 provides for such a consistent alignment of the electrodes 16a and 16b. The alignment mount 20 includes a base 22 with an arm 24 extending therefrom. The arm 24 includes a top wall 26 formed at a distal end thereof and a bottom wall 28 formed at a proximal end attached to the base 22. A sidewall 30 extends between the top wall 26 and the bottom wall 28. In the illustrative embodiment the cross sectional shape of the arm 24 is rectangular or square, however it should be noted that the cross sectional shape may include a plurality of different forms such as circular or various other polygonal configurations.

In one form, the base 22 is shaped as a tapered cup 40 with a circular top wall 42, a relatively smaller circular bottom wall 44 and a tapered side wall 46 extending therebetween. The tapered cup 40 is sized to fit within a similarly shaped well basket 17 (See FIG. 2). In various forms, the well basket 17 and the base 22 may be formed into different shapes as long as they are substantially similar to one another. A first through aperture 50 is formed in the base 22 on one side of the arm 24 and a second through aperture 52 is formed in the base 22 on another side of the arm 24. The through apertures 50, 52 permit the electrodes 16a, 16b to extend through the base 22 and into the culture medium 15 in a predetermined location controlled by the alignment mount 20. In one form the second through aperture 52 includes an optional open end 54 as shown. In other forms the second through aperture 52 is enclosed at the outer edge of the base 22. In some forms, the side wall 46 of the base 22 can include an engagement or connecting feature 60 to help retain the base 22 in a fixed location relative to the culture trey chamber 14. The engagement feature 60 can include an O-ring, locking tongue, snap fit connecting feature or other types as one skilled in the art would readily understand. In some embodiments a weight may be placed on top of the base 22 to help hold the base 22 in a desired position.

Figure 4A:
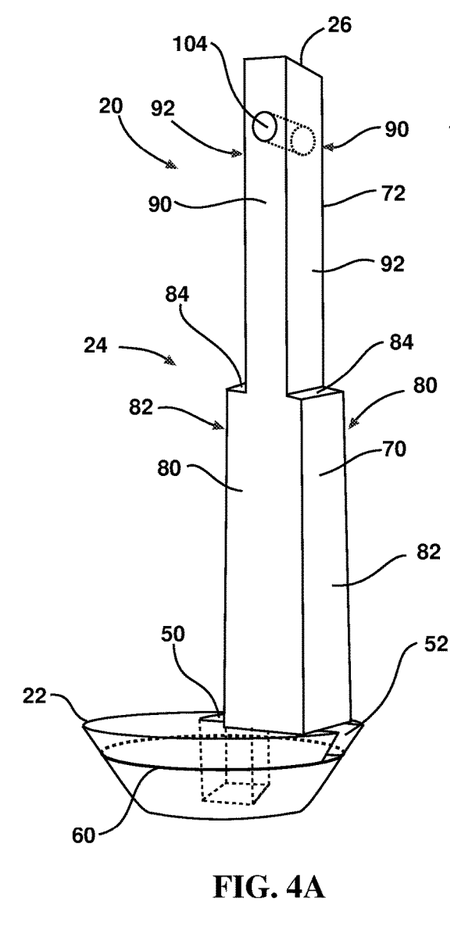
FIGS. 4A-4C are perspective views of an alignment mount according another embodiment of the present disclosure.
Figure 4B:
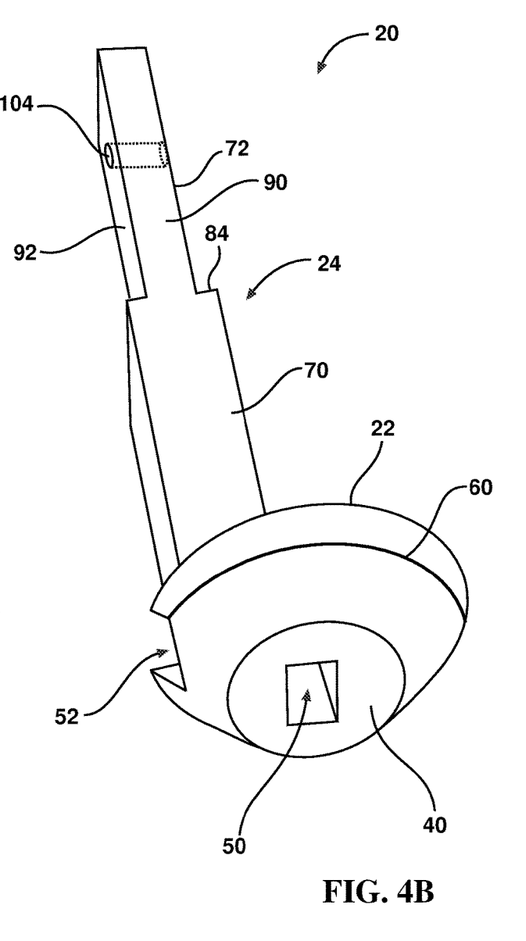
Figure 4C:
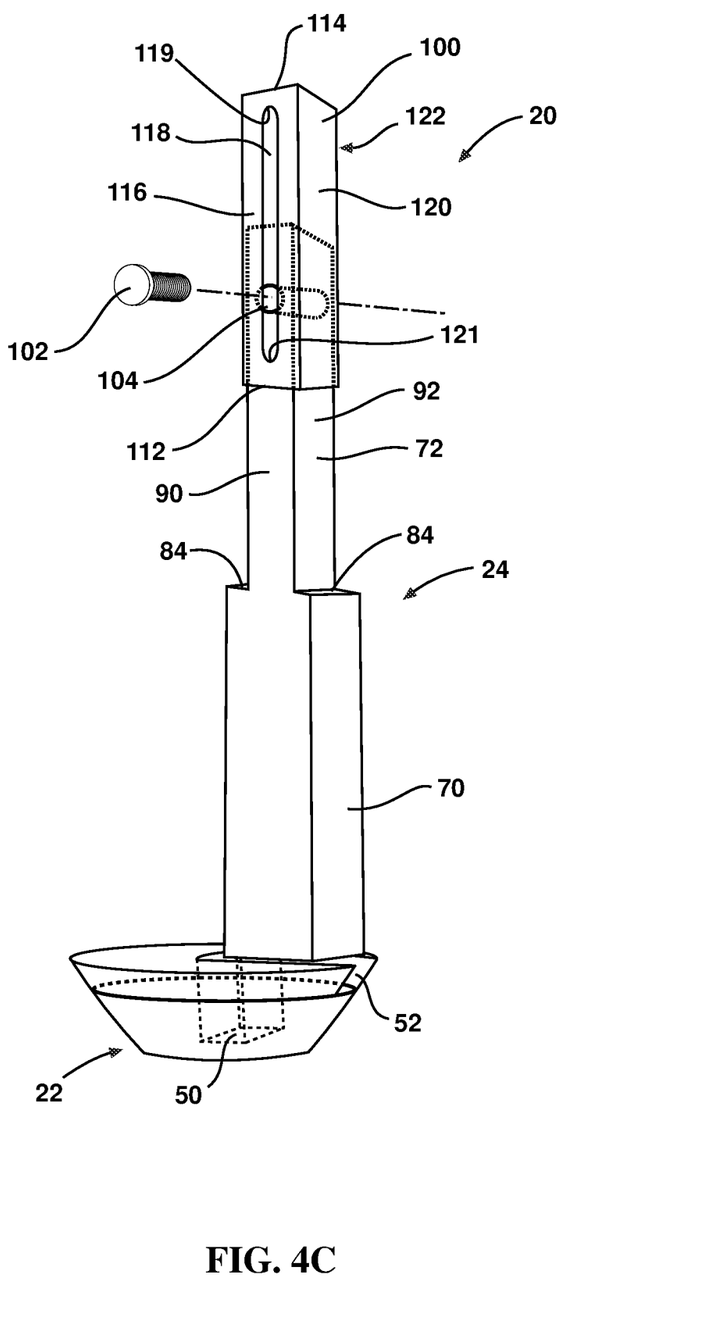

FIGS. 4A-4C are perspective views of the alignment mount 20 according another embodiment of the present disclosure wherein a variable length arm 24 is defined. Many of the features of this embodiment are substantially similar to that shown in FIGS. 3A and 3B and will not be described again. The arm 24 is defined by a first portion 70 and a second portion 72. The first portion 70 of the arm 24 is connected to and extends from the base 22. The first portion 70 can include first opposing sidewalls 80 and second opposing sidewalls 82 formed adjacent the first sidewalls 80. A shoulder 84 protrudes outward proximate the interface between first portion 70 and the second portion 72 of the arm 24. The second portion 72 can include first opposing sidewalls 90 and second opposing sidewalls 92 adjacent the first opposing sidewalls.

An adjustable sleeve 100 (see FIG. 4C) is slidingly engaged with the second portion 72 of the arm. The adjustable sleeve 100 effectively permits the length of the arm 24 to be varied to coincide with the length of the electrodes 16a, 16b, and the position or relative height of the cells 25 within the chamber 14. A threaded fastener 102 can be threadingly engaged into a threaded receiver 104 formed in the second portion 72 of the arm 24 and lock the adjustable sleeve 100 in place. It should be noted that more than one threaded fastener 102 may be used in other embodiments (not shown). Likewise, other types of mechanical fasteners such as clips, pins, clamps, etc., or others known to those skilled in the art are contemplated and may be used without departing from the teachings of the present disclosure. The adjustable sleeve 100 includes a bottom wall 112, a top wall 114 and a front wall 116 extending between the top and bottom walls 114, 112 respectively. An elongate slot 118 extending between opposing ends 119, 121 can be formed in the front wall 116 of the adjustable sleeve 100. The adjustable sleeve 100 can also include opposing sidewalls 120 and a backwall 122. It should be noted that the disclosed embodiments illustrate an arm 24 and an adjustable sleeve 100 that are substantially square or rectangular in cross sectional form, however other shapes are contemplated and remain within the teachings of this invention. By way of example and not limitation, the arm 24 and the sliding sleeve may be round or other polygonal shape. In some forms the shoulder 84 between the first and second portions 70, 72 may include an abutment for the bottom wall 112 of the adjustable sleeve 100 to limit further travel in a downward direction. In other forms, the ends 119, 121 of the adjustment slot 118 provides upper and lower abutments to limit travel of the adjustable sleeve 100 along the length thereof. Also, in alternate embodiments (not shown) the arm 24 may not have two portions (70, 72) formed in different sizes or shapes such that the adjustable sleeve 100 may slide along the length of the elongate slot 118 without respect to a shoulder portion 84 (e.g.—the adjustable sleeve 100 may slide along a single uniform sized arm 24 until abutment of either end 119, 121 of the slot 118).

The alignment mount 20 may be made from a variety of materials and manufacturing methods. The materials can include, but are not limited to metals, plastics, ceramics, composites and combinations thereof. In one form, the mount 20 can be manufactured using a 3D printer capable of printing polymer materials that are characterized by durable resin with low friction and high wear capability. It should be understood that the device can made in various sizes to correspond with differently sized culture trey chambers.

In further embodiments (not depicted), the mount 20 can be modified to include three arms 24 evenly spaced around the base 22. These arms 24 project from the base 22 and have a 90 degree turn so that when the mount 20 is placed in the culture trey chamber 14, it can be turned until these arms lock the support into place on the culture tray.

In operation, TEER electrodes 16 are positioned onto the alignment mount 20 such that the electrode abutment plate 18 is in contact with the top wall 26 of the arm 24 or the top wall 114 of the adjustable sleeve 100, depending on which type of alignment mount 20 is being used. For the adjustable version, the adjustable sleeve 100 is set to a desired location and locked into place with at least one mechanical fastener or clip 102. The alignment mount 20 and electrodes 16 are then moved to the culture tray such that the base 22 is inserted into one of the chambers 14. The alignment mount 20 ensures that the electrodes 16*a* and 16*b* are located in the correct position in repeatable fashion with respect to the cells 25 in the upper chamber 21 and the culture medium in the lower chamber 23. Electrical measurements of the cells 25 can then be made and recorded such that they can be compared with measurements of other cell cultures with accuracy and precise repeatability in order to further scientific research and analysis in this area of technology.

In one aspect, the present disclosure includes an electrode alignment mount comprising: a base having a top wall, a bottom wall and a side wall extending between the top wall and bottom wall configured in a shape substantially similar to a shape of a culture trey chamber; and an elongate support arm extending from the top wall of the base to a distal end thereof.

In refining aspects, the elongate arm includes a first portion having a first cross sectional area connected to the base and a second portion having a second relatively smaller cross sectional area extending from the first portion to the distal end; wherein the cross sectional shape of the first and second portions is one of rectangular, circular, or polygonal; wherein the cross-sectional shape of the first and second portions are different from one another; further comprising a sleeve slidingly engageable along a portion of the elongate arm to vary the length thereof; wherein the sleeve includes an elongate slot extending along a length of a wall thereof; wherein the support arm includes a threaded receiver formed in a wall thereof; further comprising a threaded fastener positioned through the elongate slot of the sleeve and threadingly engageable with the threaded receiver wherein the sleeve is releasably lockable at a desired position on the support arm with the threaded fastener; wherein the base is positioned within a culture trey chamber; wherein the top wall and bottom wall of the base include a circular shape; wherein the side wall of the base is inwardly tapered from the top wall to the bottom wall; further comprising an engagement feature positioned circumferentially around the side wall configured to engage a wall of a culture trey chamber; wherein the engagement feature is one of an O-ring, locking tongue, snap fit connecting feature or other releasable locking element; further comprising a first through aperture and a second through aperture extending through the base adjacent opposing sides of the arm; further comprising positioning a pair of TEER electrodes adjacent a distal end of the arm such that the electrodes extend through the each of the first and second through apertures of the base.

In another aspect, the present disclosure includes a TEER measurement system comprising: an alignment mount having a base and an arm extending from the base; an electrode device coupled to the alignment mount; and a culture tray having a culture tray chamber configured to receive the base of the alignment mount and electrodes of the electrode device.

In refining aspects the TEER measurement system further comprises a sleeve slidingly engageable with the arm to adjust a length thereof; an elongate slot formed in a side wall of the sleeve; a threaded fastener positioned through the slot being threadingly engageable with a threaded aperture formed in the arm; wherein the base includes a first through aperture positioned on one side of the arm and a second through aperture positioned on an opposing side of the arm.

In another aspect, A TEER electrode alignment mount comprises: a base having a top wall, a bottom wall and a sidewall shaped to fit within a culture tray chamber; an engagement feature formed in the sidewall of the base; an extension arm projecting from a top wall of the base; and first and second through apertures formed in the base on opposing sides of the arm configured to receive first and second electrodes therethrough, respectively.

In refining aspects, the TEER electrode alignment mount further comprises: an adjustable sliding sleeve selectively locked in a desired location on the extension arm.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

What is claimed is:

1. An electrode alignment mount comprising:
   a base having a top wall, a bottom wall and a conical side wall extending 360 degrees around between the top wall and bottom wall configured in a shape substantially similar to a shape of a basket positioned in a culture tray chamber;
   an elongate support arm extending from the top wall of the base to a distal end thereof; and
   wherein the base is constructed and arranged to be placed within the basket such that the conical side wall of the base engages with a side wall of the basket around a perimeter thereof to hold the elongate support arm in a fixed position with respect to the basket.

2. The electrode alignment mount of claim 1, wherein the elongate arm includes a first portion having a first cross sectional area connected to the base and a second portion having a second relatively smaller cross sectional area extending from the first portion to the distal end.

3. The electrode alignment mount of claim 2, wherein the cross sectional shape of the first and second portions is one of rectangular, circular, or polygonal.

4. The electrode alignment mount of claim 2, wherein the cross-sectional shape of the first and second portions are different from one another.

5. The electrode alignment mount of claim 1, further comprising a sleeve slidingly engageable along a portion of the elongate arm to vary the length thereof.

6. The electrode alignment mount of claim 5, wherein the sleeve includes an elongate slot extending along a length of a wall thereof.

7. The electrode alignment mount of claim 6, wherein the support arm includes a threaded receiver formed in a wall thereof.

8. The electrode alignment mount of claim 7, further comprising a threaded fastener positioned through the elongate slot of the sleeve and threadingly engageable with the threaded receiver.

9. The electrode alignment mount of claim 8, wherein the sleeve is releasably lockable at a desired position on the support arm with the threaded fastener.

10. The electrode alignment mount of claim 1, wherein the top wall and bottom wall of the base include a circular shape.

11. The electrode alignment mount of claim 1, wherein the side wall of the base is inwardly tapered from the top wall to the bottom wall.

12. The electrode alignment mount of claim 1, further comprising an engagement feature positioned circumferentially around the sidewall configured to engage a wall of the well basket in the chamber.

13. The electrode alignment mount of claim 12, wherein the engagement feature is one of an O-ring, locking tongue, snap fit connecting feature or other releasable locking element.

14. The electrode alignment mount of claim 1, further comprising a first through aperture and a second through aperture extending through the base adjacent opposing sides of the arm.

15. The electrode alignment mount of claim 14, further comprising positioning a pair of transepithelia/transendothelial electrical resistance (TEER) electrodes adjacent a distal end of the arm such that the electrodes extend through the each of the first and second through apertures of the base.

16. An electrode alignment mount comprising:
 a base having a top wall, a bottom wall and a conical side wall extending between the top wall and bottom wall configured in a shape substantially similar to a shape of a well basket in a culture of a multi-culture tray chamber;
 an elongate support arm extending from the top wall of the base to a distal end above the base;
 a first through aperture formed through the base top wall and bottom wall on one side of the elongate arm;
 a second through aperture formed through the base top wall and bottom wall on another side of the elongate arm; and
 wherein a first transepithelia/transendothelial electrical resistance (TEER) electrode and a second (TEER) electrode are spaced apart from the elongate arm, positioned on opposing sides of the elongate arm and extend through the first and the second through apertures of the base, respectively.

* * * * *